(12) United States Patent
Kasuga et al.

(10) Patent No.: US 10,814,000 B2
(45) Date of Patent: *Oct. 27, 2020

(54) GUIDED BONE REGENERATION MEMBRANE AND MANUFACTURING METHOD THEREOF

(71) Applicants: NATIONAL UNIVERSITY CORPORATION NAGOYA INSTITUTE OF TECHNOLOGY, Nagoya-shi, Aichi (JP); YABASHI INDUSTRIES, CO., LTD., Oagaki-shi, Gifu (JP); YAMAHACHI DENTAL MFG., CO., Gamagori, Aichi (JP); ORTHOREBIRTH CO., LTD., Yokohama-shi, Kanagawa (JP)

(72) Inventors: Toshihiro Kasuga, Aichi-ken (JP); Yoshio Ota, Gifu-ken (JP); Takashi Wakita, Aichi-Ken (JP)

(73) Assignees: NATIONAL UNIVERSITY CORPORATION NAGOYA INSTITUTE OF TECHNOLOGY, Nagoya-shi, Aichi (JP); ORTHOREBIRTH CO., LTD., Yokohama-shi, Kanagawa (JP); YAMAHACHI DENTAL MFG., CO., Gamagori, Aichi (JP); YABASHI INDUSTRIES, CO., LTD., Oagaki-shi, Gifu (JP)

( * ) Notice: Subject to any disclaimer, the term of this patent is extended or adjusted under 35 U.S.C. 154(b) by 46 days.

This patent is subject to a terminal disclaimer.

(21) Appl. No.: 16/227,582

(22) Filed: Dec. 20, 2018

(65) Prior Publication Data

US 2019/0117774 A1    Apr. 25, 2019

Related U.S. Application Data

(60) Continuation of application No. 16/119,601, filed on Aug. 31, 2018, now Pat. No. 10,159,737, which is a division of application No. 14/270,137, filed on May 5, 2014, now Pat. No. 10,092,650, which is a division of application No. 13/592,072, filed on Aug. 22, 2012, now abandoned, which is a continuation-in-part of application No. 12/591,258, filed on Nov. 13, 2009, now abandoned.

(51) Int. Cl.
*A61K 47/02* (2006.01)
*A61L 31/06* (2006.01)
*A61L 31/12* (2006.01)
*A61L 31/14* (2006.01)
*A61K 33/00* (2006.01)
*C08L 67/04* (2006.01)

(52) U.S. Cl.
CPC .............. *A61K 47/02* (2013.01); *A61K 33/00* (2013.01); *A61L 31/06* (2013.01); *A61L 31/128* (2013.01); *A61L 31/148* (2013.01); *C08L 67/04* (2013.01); *A61L 2430/02* (2013.01)

(58) Field of Classification Search
None
See application file for complete search history.

(56) References Cited

U.S. PATENT DOCUMENTS 10,092,650 B2 * 10/2018 Kasuga ................. A61L 31/128
10,159,737 B1 * 12/2018 Kasuga ................. A61L 31/148

OTHER PUBLICATIONS

Fujihara et al, "Guided bone regeneration membrane made of polycaprolactone/calcium carbonate composite nano-fibers," Biomaterials, vol. 26, No. 19, pp. 4139-4147 (Year: 2005).*

Kikuchi et al, "Development of guided bone regeneration membrane composed of β-tricalciunn phosphate and poly (L-lactide-co-glycolide-co-ε-caprolactone) composites," Biomaterials, vol. 25, Issue 28, pp. 5979-5986 (Year: 2004).*

Maeda et al, "Preparation of poly(L-lactic acid)-polysiloxane-calcium carbonate hybrid membranes for guided bone regeneration," Biomaterials, vol. 27, No. 8, pp. 1216-1222 (Year: 2006).*

Hotta et al, "Preparation of poly(lactic acid) microfiber mats containing calcium carbonate particles by an electrospinning method," 11th Symposium on Ceramics in Medicine, Biology and Biomimetics, p. 15 (Year: 2007).*

* cited by examiner

*Primary Examiner* — Dennis J Parad
(74) *Attorney, Agent, or Firm* — Osha Liang LLP

(57) ABSTRACT

A guided bone regeneration material is disclosed. The guided bone regeneration material includes biodegradable fibers produced by an electrospinning method. The biodegradable fibers produced by the method include a silicon-releasing calcium carbonate and a biodegradable polymer. The silicon-releasing calcium carbonate is a composite of siloxane and calcium carbonate of vaterite phase. The biodegradable fibers may be coated with apatite. When the guided bone regeneration material is immersed in a neutral aqueous solution, silicon species ions are eluted from the calcium carbonate. The guided bone regeneration material excels in bone reconstruction ability.

12 Claims, 8 Drawing Sheets

GUIDED BONE REGENERATION MEMBRANE AND MANUFACTURING METHOD THEREOF

CROSS REFERENCE TO RELATED APPLICATIONS

This is a continuation application of U.S. application Ser. No. 16/119,601, filed on Aug. 31, 2018, which is a divisional application of U.S. application Ser. No. 14/270,137, filed on May 5, 2014, which is a divisional application of U.S. application Ser. No. 13/592,072, field on Aug. 22, 2012, which is a continuation-in-part application of U.S. application Ser. No. 12/591,258 filed on Nov. 13, 2009. This application claims the benefits and priority of all these prior applications and incorporates the disclosures of these prior applications by reference in their entireties.

FIELD OF THE INVENTION

The present invention relates to a guided bone regeneration material and a manufacturing method thereof. The guided bone regeneration material is used in a guided bone regeneration (GBR) technique which is a technique for repairing bone defects and is widely used in the field of oral surgery and maxillofacial surgery.

RELATED ART OF THE INVENTION

Guided bone regeneration membrane is a masking membrane that covers bone defect areas so as to prevent invasion of non-osteogenesis-contributing cells and tissues into the bone defect areas and to allow the bone to reconstruct by taking full advantage of the self-regenerative power thereof. Guided bone regeneration techniques using these membranes can cure bone defects by using a healing potential which the living body inherently has. The techniques are not complicated in their operative procedures and have given many satisfactory outcomes in oral surgery.

Guided bone regeneration membranes may be broadly grouped under non-bioresorbable membrane and bioresorbable membrane. A polytetrafluoroethylene (expanded polytetrafluoroethylene; ePTEF) has been practically used as a material for a non-bioresorbable membrane, from which good clinical data have been obtained. This material, however, places a not-so light burden on a patient, because it is not bioresorbable and thereby needs a secondary operation for the removal of the membrane after the target bone defect area is repaired. In addition, it is difficult to adopt this material to a large defect area, because the material is bioinert (non-bioresorbable). In contrast, use of guided bone regeneration membrane that are bioresorbable can avoid the surgical stress caused by the secondary operation. Exemplary materials for such bioresorbable guided bone regeneration membrane include poly(lactic acid)s as bioresorbable synthetic polyesters; and copoly(lactic acid/glycolic acid)s; and collagens and fasciae each of biological origin. Such bioresorbable guided bone regeneration membrane have been recently investigated and developed heavily, and some of them have already been commercialized. Typically, there have been proposed a wide variety of guided bone regeneration membrane and manufacturing methods thereof; such as a bone regeneration membrane including a composite of a bioresorbable polymer with tricalcium phosphate or hydroxyapatite and having micropores (Japanese Unexamined Patent Application Publication (JP-A) No. H06 (1994)-319794); a protective membrane including a felt made from a bioresorbable material (Japanese Unexamined Patent Application Publication (JP-A) No. H07 (1995)-265337; and Japanese Unexamined Patent Application Publication (JP-A) No. 2004-105754); a multilayer membrane including a sponge-like collagen matrix layer and a relatively impermeable barrier layer (Japanese Unexamined Patent Application Publication (Translation of PCT Application) (JP-A) No. 2001-519210); a bioresorbable tissue regeneration membrane for dental use, which has a porous sheet-like structure including a polymer blend containing two or more different bioresorbable polymers (Japanese Unexamined Patent Application Publication (JP-A) No. 2002-85547); a resorbable flexible implant in the form of a continuous micro-porous sheet (Japanese Unexamined Patent Application Publication (Translation of PCT Application) (JP-A) No. 2003-517326); and a biocompatible membrane prepared by three-dimensional powder sinter molding through application of laser light to a biodegradable polymer powder (Japanese Unexamined Patent Application Publication (JP-A) No. 2006-187303).

In particular, oral or maxillary bone defects should be desirably cured as soon as possible, because it is very important to maintain and ensure mastication for the health maintenance in a super-graying society. To improve osteogenic ability, there have been attempts to incorporate a factor such as an osteogenesis inducer (Japanese Unexamined Patent Application Publication (JP-A) No. H06 (1994)-319794), a growth factor or a bone morphogenic protein (Japanese Unexamined Patent Application Publication (Translation of PCT Application) (JP-A) No. 2001-519210; and Japanese Unexamined Patent Application Publication (JP-A) No. 2006-187303) in a bioresorbable membrane. However, it is difficult to handle these factors. Accordingly, there is a need to develop a bioresorbable guided bone regeneration material having superior bone reconstruction ability to allow the bone to self-regenerate more reliably and more rapidly.

In view of recent trends of researches and technologies for bio-related materials, the main stream of researches has shifted from a material design for the bonding of a material with the bone to a material design for the regeneration of a real bone. In these researches, the role of silicon in osteogenesis has received much attention, and a variety of materials containing silicon have been designed (TSURU Kanji, OGAWA Tetsuro, and OGUSHI Hajime, "Recent Trends of Bioceramics Research, Technology and Standardization," Ceramics Japan, 41, 549-553 (2006)).

For example, it has been reported that the controlled release of silicon can act on cells to promote osteogenesis (H. Maeda, T. Kasuga, and L. L. Hench, "Preparation of Poly(L-lactic acid)-Polysiloxane-Calcium Carbonate Hybrid Membranes for Guided Bone Regeneration," Biomaterials, 27, 1216-1222 (2006)). Independently, when composites of a poly(lactic acid) with one of three calcium carbonates (calcite, aragonite, and vaterite) are soaked in a simulated body fluid (SBF), the composite of a poly(lactic acid) with vaterite forms a bone-like apatite within a shortest time among the three composites (H. Maeda, T. Kasuga, M. Nogami, and Y Ota, "Preparation of Calcium Carbonate Composite and Their Apatite-Forming Ability in Simulated Body Fluid", J. Ceram. Soc. Japan, 112, S804-808 (2004)).

These findings demonstrate that the use of vaterite which gradually releases silicon is believed to be a key to provide a guided bone regeneration material that gives rapid bone reconstruction. Inventors of the present invention have already disclosed silicon-releasing calcium carbonate of vaterite phase and a production method thereof in JP Application No. 2006-285429 (JP publication No. 2008-1000878).

SUMMARY OF THE INVENTION

An object of the present invention is to provide a bioresorbable guided bone regeneration material that is capable of effectively inducing a bone reconstruction ability. Another object of the present invention is to provide a method for manufacturing a guided bone regeneration material of high performance (achieving rapid bone reconstruction) in an inexpensive and industrially advantageous manner.

The present invention provides, in an embodiment, a fibrous guided bone regeneration material which contains a silicon-releasing calcium carbonate and a biodegradable polymer, such as poly(lactic acid). The fibrous material may be coated with an apatite.

The present invention provides, in an embodiment, a fibrous guided bone regeneration material that may have a bi-layered structure, which includes a first nonwoven fabric layer and a second nonwoven fabric layer. The first nonwoven fabric layer contains a silicon-releasing calcium carbonate and a biodegradable polymer, such as poly(lactic acid) (PLA) as principal components (hereinafter referred to as "Si—CaCO$_3$/PLA layer"). The second nonwoven fabric layer contains biodegradable polymer, such as PLA as a principal component (hereinafter referred to as "PLA layer"). In the bi-layer structured guided bone regeneration membrane, the PLA layer has the function of preventing the invasion of soft tissues, and the apatite-coated Si—CaCO3/PLA layer has the function of improving cellular affinity and/or osteogenic ability.

In another embodiment, a technique of manufacturing a nonwoven fabric through electrospinning is adopted to the manufacturing of such a guided bone regeneration material. This provides an easy manufacturing of a material that has continuous pores for supplying nutrients to cells and shows improved fitting ability to an affected area. Such a bioresorbable apatite that improves cellular initial adhesion can be easily applied to the fibrous material containing silicon-releasing calcium carbonate and PLA by soaking the fibrous material in a simulated body fluid (SBF).

The guided bone regeneration material according to the present invention shows high cellular growth ability in cellular affinity tests using osteoblastic cells (MC3T3-E1 cells) and is expected as a bioresorbable guided bone regeneration material that excels in bone reconstruction ability. The method according to the present invention can easily and efficiently manufacture a guided bone regeneration material having the above possibility.

BRIEF DESCRIPTION OF THE DRAWINGS

Other objects, features and advantages of the present invention will be understood more fully from the following detailed description made with reference to the accompanying drawings. In the drawings.

DETAILED DESCRIPTION OF THE PREFERRED EMBODIMENTS

Figure 1:
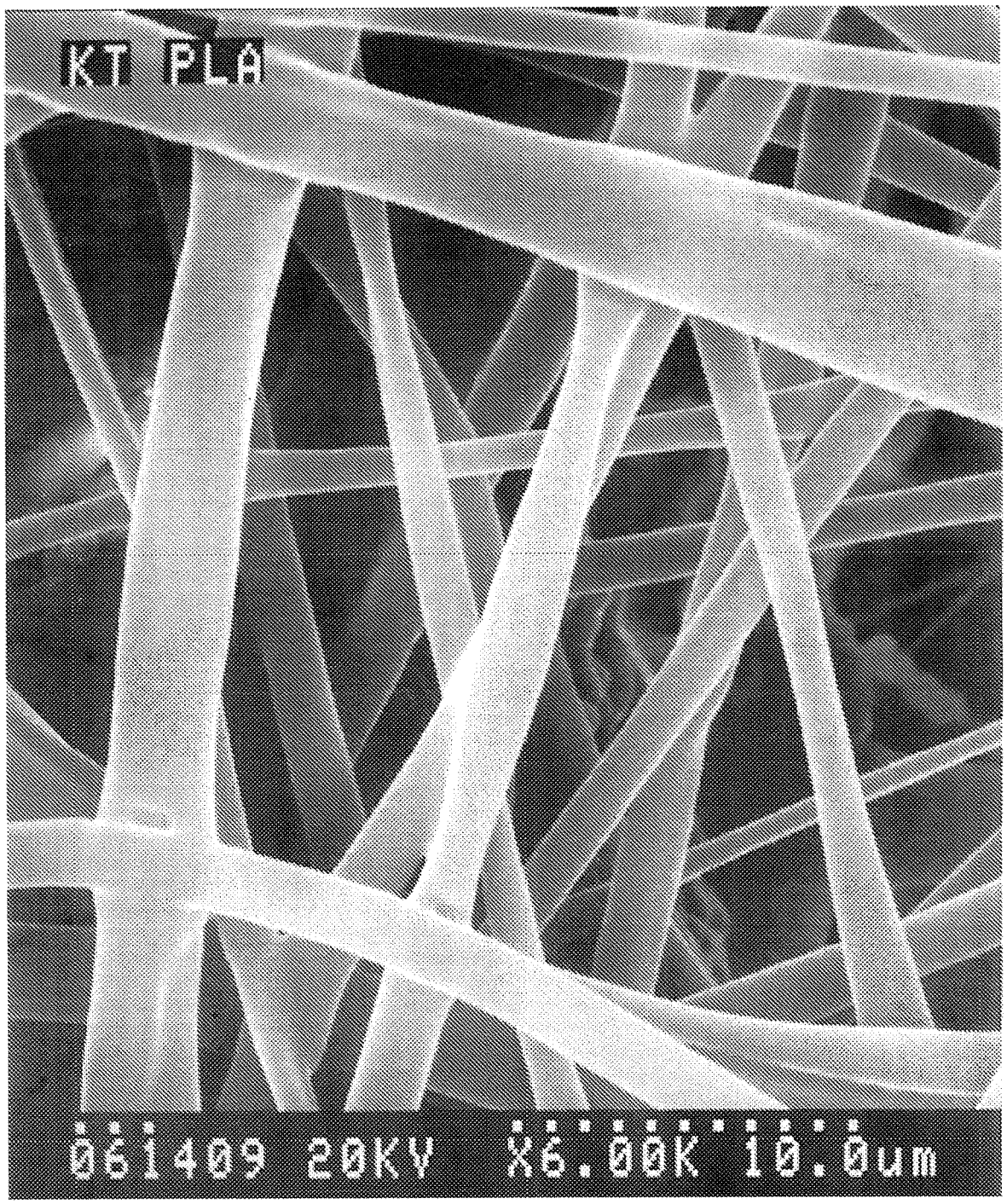
FIG. 1 is a scanning electron micrograph (SEM photograph) of a PLA layer surface of a guided bone regeneration membrane prepared in Example 1.

Embodiments of the invention relate to bone regeneration materials that comprise biodegradable fibers that comprise a biodegradable polymer and a silicon-releasing calcium carbonate. A silicon-releasing calcium carbonate is a calcium carbonate that contains releasable silicon. Embodiments of the present invention will be further illustrated with the following examples, with reference to various embodiments in the drawings. One skilled in the art would appreciate that these examples are for illustration only and other modifications and variations are possible without departing from the scope of the invention.

According to a preferred embodiment of the present invention, a guided bone regeneration material may be manufactured through the steps of electrospinning and soaking in a simulated body fluid (SBF). In the electrospinning step, a positive high voltage may be applied to a polymer solution, and the resulting polymer solution is sprayed as fibers to a negatively charged collector.

To produce biodegradable materials of the present invention, a spinning solution may be prepared by dissolving a biodegradable polymer in an appropriate solvent, such as poly(lactic acid) in chloroform (CHCl$_3$) or dichloromethane (DCM). In accordance with embodiments of the invention, a spinning solution may have a poly(lactic acid) concentration of, for example, from 4 to 12 percent by weight for easy spinning. In this description, any numerical range is meant to include all numbers therebetween, as if all numbers therebetween have been individually disclosed. In this connection, the poly(lactic acid) (PLA) preferably may have a molecular weight of from about $20 \times 10^4$ to about $30 \times 10^4$. However, PLAs with molecular weights outside this range may also be used. To maintain conditions for satisfactory spinning, the spinning solution may further contain other solvents, such as dimethylformamide (DMF) and/or methanol (CH$_3$OH) in a selected amount, such as up to about 50 percent by weight relative to the amount of CHCl$_3$ or DCM.

A spinning solution for the formation of a guided bone regeneration (GBR) material of the present invention may be prepared by adding a powder of silicon-releasing calcium material (e.g., calcium carbonate) to the PLA spinning solution. The silicon-releasing calcium carbonate may be added to the solution such that the content of the silicon-releasing calcium carbonate may be from 40 to 60 percent by weight. This allows an apatite to deposit efficiently on the electrospun fibers in the SBF soaking step. Alternatively, a spinning solution for the formation of a guided bone regeneration material may be prepared by kneading a poly(lactic acid) and silicon-releasing calcium carbonate in predetermined proportions, using a heating kneader to give a composite, followed by dissolving the composite in a solvent.

In a GBR material of the present invention, a silicon-releasing calcium carbonate to be mixed with PLA may be formed of a composite of siloxane and calcium carbonate, wherein the calcium carbonate may be of vaterite phase. A composite of siloxane and calcium carbonate may be prepared by a carbonation process described in Japanese Patent Application No. 2006-285429 (corresponding to Japanese Unexamined Patent Application Publication (JP-A) No. 2008-100878), the disclosure of which is incorporated herein by reference. In the carbonation process, carbon dioxide is blown into a suspension prepared by mixing methanol, slaked lime, and an organic silicon compound. Upon stirring the mixture and blowing carbon dioxide, gelation occurs with the suspension. Product material of the gelation of the suspension may be suction filtered and dried to obtain powders of silicon-releasing calcium carbonate.

The powders of silicon-releasing calcium carbonate may be formed of spherical particles having an average diameter of about 1 μm. A content of the silicon doped in the calcium carbonate may be adjusted depending on the amounts and ratios of methanol, slaked lime and an organic silicon compound in the suspension. Preferably, the silicon content is about 0.5-5 wt %, more preferably 1-5 wt %, and most preferably about 2 wt %.

Upon immersing a silicon-releasing calcium carbonate in a neutral aqueous solution, such as distilled water or a phosphate buffered saline, silicon species ions may be separated from the silicon-releasing calcium carbonate and be eluted into the solution together with calcium ions. In this description, silicon-releasing calcium carbonate will be sometimes referred to as Si—$CaCO_3$.

A biodegradable polymer of a guided bone regeneration material of the present invention preferably contains a poly(lactic acid) (PLA) by itself or as a copolymer, such as a copolymer of poly (lactic acid) and poly(glycolic acid) (PGA), i.e., (copoly(lactic acid/glycolic acid)). Examples of other biodegradable polymers usable with embodiments of the invention may include synthetic polymers such as polyethylene glycols (PEGS), polycaprolactones (PCLs), as well as copolymers among lactic acid, glycolic acid, ethylene glycol, and/or caprolactone; and natural polymers such as fibrin, collagens, alginic acids, hyaluronic acids, chitins, and chitosans.

A fibrous material formed of Si—$CaCO_3$ and PLA may further contain inorganic substances that are usable without biological problems. Examples of such inorganic substances include tricalcium phosphate, calcium sulfate, sodium phosphate, sodium hydrogenphosphate, calcium hydrogenphosphate, octacalcium phosphate, tetracalcium phosphate, calcium pyrophosphate, and calcium chloride.

Using an electrospinning apparatus, a spinning solution is charged and sprayed from a nozzle, converted into fibers (thin streams) in an electric field while evaporating the solvent. The charged fibers are jetted toward a collector connected with a negative electrode to form a thin layer of fibers on the collector. A desired guided bone regeneration membrane may be prepared by changing spinning conditions, such as concentrations, solvent types, supply speeds (feed rates) of the spinning solutions, spinning times, applied voltages, and the distance between the nozzle and the collector. The prepared nonwoven fabrics may be pressed so as to be compacted or to have a desired thickness.

A guided bone regeneration membrane having a bi-layered structure may be produced by spraying a PLA spinning solution to form a PLA layer, followed by spraying a Si—$CaCO_3$/PLA spinning solution to form a Si—$CaCO_3$/PLA layer on the PLA layer. Alternatively, a bi-layer structure may be prepared by producing a PLA nonwoven fabric and a Si—$CaCO_3$/PLA nonwoven fabric independently, followed by combining the two nonwoven fabrics.

A guided bone regeneration membrane having a bi-layered structure may be cut to a desired size and soaked in a simulated body fluid (SBF) or a solution with 1.5 times higher concentration of inorganic ions compared to SBF (1.5SBF) at about 37° C. for a predetermined time to precipitate an apatite on the Si—$CaCO_3$/PLA layer. This gives a bioresorbable guided bone regeneration membrane including a novel mechanism that can effectively induce the bone reconstruction.

A simulated body fluid (SBF) is an acellular fluid that has inorganic ion concentrations similar to those of human extracellular fluid. A SBF may be used to reproduce formation of apatite on bioactive materials in vitro. See, Kukubo et al., "*Apatite formation on ceramics, metal, and polymers induced by a CaO SiO2 based glass in a simulated body fluid,*" in Bioceramics, W. Bonfield, G. W. Hastings, and K. E. Tanner, Eds. 1991, Buttrworth-Heinemann: Oxford.

The SBF soaking can be performed even after combining (or laminating) the two layers. Even in this case, the apatite does not appreciably deposit on the PLA layer, but selectively on the Si—$CaCO_3$/PLA layer. This is because silicon contained in the Si—$CaCO_3$/PLA layer can induce nucleation of apatite, and the calcium component continues to precipitate out to increase the degree of supersaturation of apatite around the nucleation sites. As a result, apatite selectively deposits on the surface of the Si—$CaCO_3$/PLA layer, but not on the surface of the PLA layer, which is hydrophobic and not conducive to the deposition of apatite.

EXAMPLES

Example 1

Manufacturing methods of guided bone regeneration membranes according to embodiments of the present invention will be illustrated with reference to several examples below. It should be noted, however, that these examples are included merely to aid in the understanding of the present invention and are not to be construed to limit the scope of the present invention.

Raw materials used in the examples are as follows:

Silicon-releasing calcium carbonate (Si—$CaCO_3$): Calcium carbonate of vaterite phase having a silicon content of 2.9 wt % prepared by using slaked lime (Microstar T; purity 96% or more; Yabashi Industries Co., Ltd., Japan), methanol (analytical grade reagent; purity 99.8% or more; Kishida Chemical Co., Ltd., Japan), γ-aminopropyltriethoxysilane (TSL 8331; purity 98% or more; GE Toshiba Silicones Co., Ltd., Japan), and carbon dioxide gas (high-purity liquefied carbon dioxide gas; purity 99.9%; Taiyo Kagaku Kogyo K.K.);

Poly(lactic acid) (PLA): PURASORB PL Poly(L-lactide), molecular weight of $20\times10^4$ to $30\times10^4$, PURAC Biochem;

Chloroform ($CHCl_3$): Analytical grade reagent, purity 99.0% or more, Kishida Chemical Co., Ltd., Japan;

N,N-Dimethylformamide (DMF): Analytical grade reagent, purity 99.5% or more, Kishida Chemical Co., Ltd., Japan.

A PLA spinning solution having a PLA content of 6.8 wt % was prepared by mixing 10 g of PLA, 110 g of $CHCl_3$, and 27.5 g of DMF. Separately, a Si—$CaCO_3$/PLA spinning solution having a Si—$CaCO_3$ content of 7.5 wt % and a PLA content of 5.0 wt % was prepared by mixing 15 g of Si-CaCO$_3$, 10 g of PLA, 140 g of CHCl$_3$, and 35 g of DMF. Using the prepared spinning solutions, a guided bone regeneration membrane having a bi-layered structure of nonwoven fabrics was manufactured by electrospinning.

PLA Layer Preparation Conditions

In this example, the spinning solution feed rate is about 0.1 ml/min., the applied voltage is 15 kV, the distance between the nozzle and collector is 10 cm. The nozzle laterally moves in a width of 3 to 4 cm at a rate of 15 cm/min, and a conveyor-type collector (conveyor speed: 5 to 6 m/min) is used. A spinning time is about 170 minutes.

Si—CaCO$_3$/PLA Layer Preparation Conditions

In this example, the spinning solution feed rate is about 0.16 ml/min, the applied voltage is 20 kV, the distance between the nozzle and collector is 10 cm, and the nozzle laterally moves in a width of 3 to 4 cm at a rate of 15 cm/min. A conveyor-type collector (conveyor speed: 5 to 6 m/min) is used. A spinning time is about 130 minutes.

Figure 2:
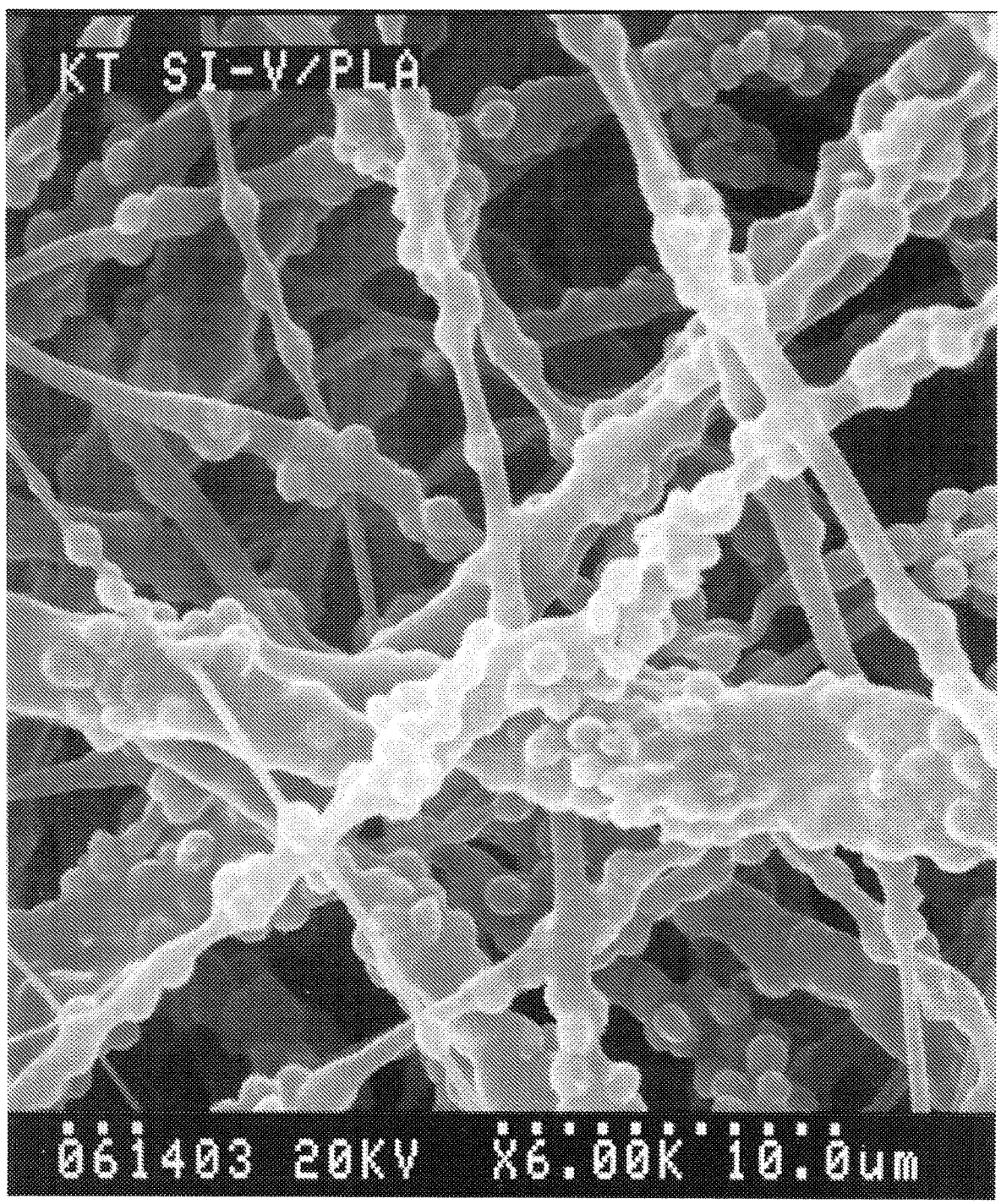
FIG. 2 is a scanning electron micrograph of a Si—CaCO$_3$/PLA layer surface of the guided bone regeneration membrane prepared in Example 1.

The microstructure of a PLA layer thus prepared (the side for preventing soft tissue invasion) is shown in the scanning electron microscope (SEM) photograph of FIG. 1. The microstructure of the Si—CaCO$_3$/PLA layer (the side for bone regeneration) is shown in the scanning electron micrograph of FIG. 2, demonstrating that Si—CaCO$_3$ particles are attached to the PLA fibers.

Example 2

A spinning solution having a PLA content of 9.0 wt % was prepared by mixing 9 g of PLA and 91 g of CHCl$_3$. Using this spinning solution, a PLA layer was prepared by electrospinning.

PLA Layer Preparation Conditions

In this example, the spinning solution feed rate is 0.05 ml/min, the applied voltage is 20 kV, and the distance between the nozzle and collector is 15 cm. The nozzle is fixed, so is the plate collector. The spinning time is 60 minutes.

Separately, PLA and Si—CaCO$_3$ were kneaded in a heating kneader at 200° C. for 15 minutes to give a Si—CaCO$_3$/PLA composite containing 60 wt % of Si—CaCO$_3$. A spinning solution having a Si—CaCO$_3$ content of 13.0 wt % and a PLA content of 8.7 wt % was prepared by mixing 25 g of the Si—CaCO$_3$/PLA composite and 90 g of CHCl$_3$. Using this spinning solution, a Si—CaCO$_3$/PLA layer was prepared by electrospinning.

Si—CaCO$_3$/PLA Layer Preparation Conditions

In this example, the spinning solution feed rate is 0.05 ml/min, the applied voltage is 20 kV, and the distance between the nozzle and collector is 15 cm. A fixed nozzle and a fixed plate collector are used. The spinning time is 30 minutes.

The two nonwoven fabrics prepared by the above procedures were each cut into a desired size and affixed or combined with each other to form a membrane. To combine two layers to form a membrane, for example, a PLA layer may be laid over a Si—CaCO$_3$/PLA layer, and a stainless steel mesh (40-mesh) may be laid over the PLA layer. A plate heated at 150° C. to 160° C. may be placed on the stainless steel mesh and pressed under a suitable pressure for about 10 seconds to produce a combined membrane (composite membrane).

Figure 3:
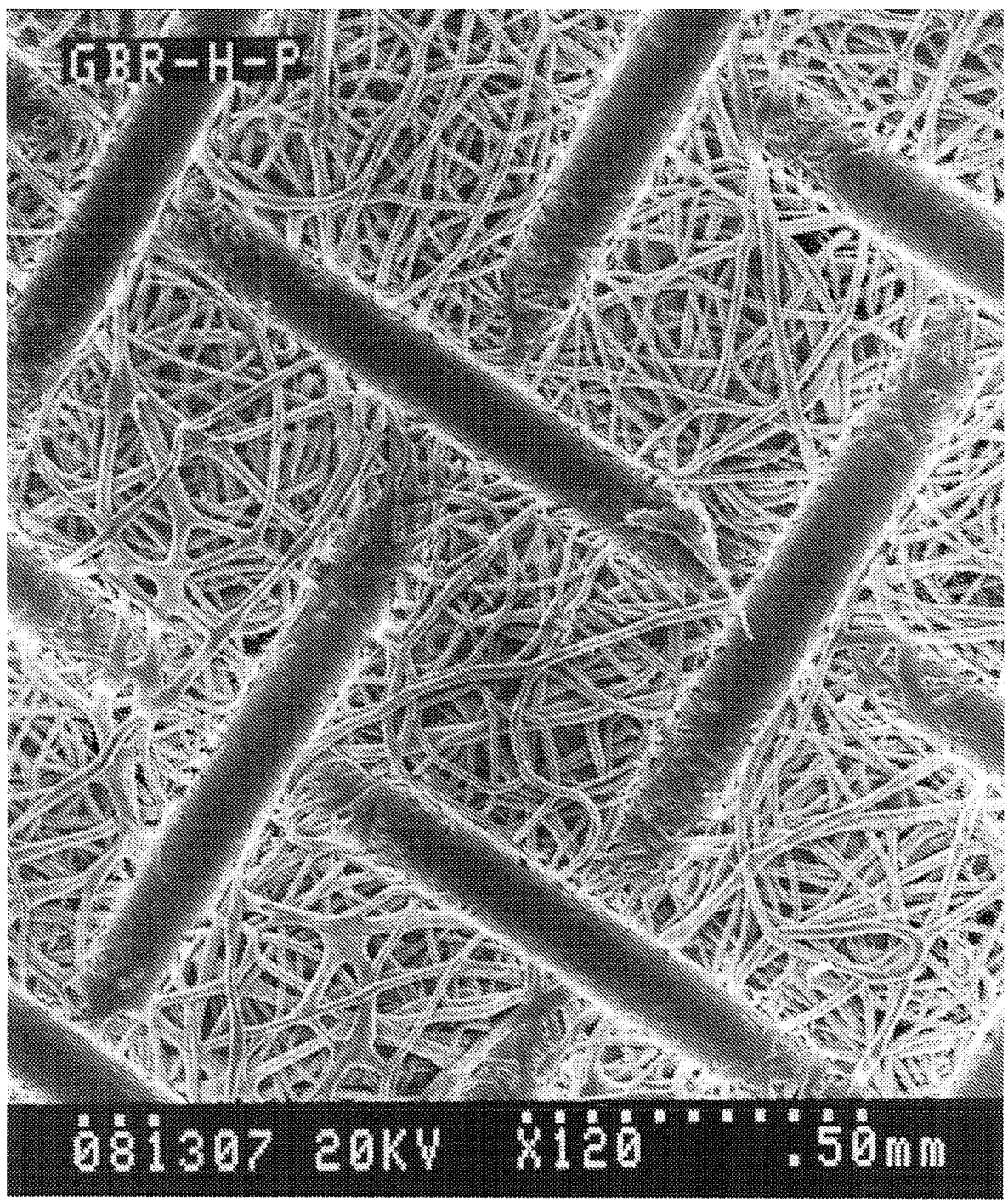
FIG. 3 is a scanning electron micrograph of a surface of a PLA layer prepared in Example 2.
Figure 4:
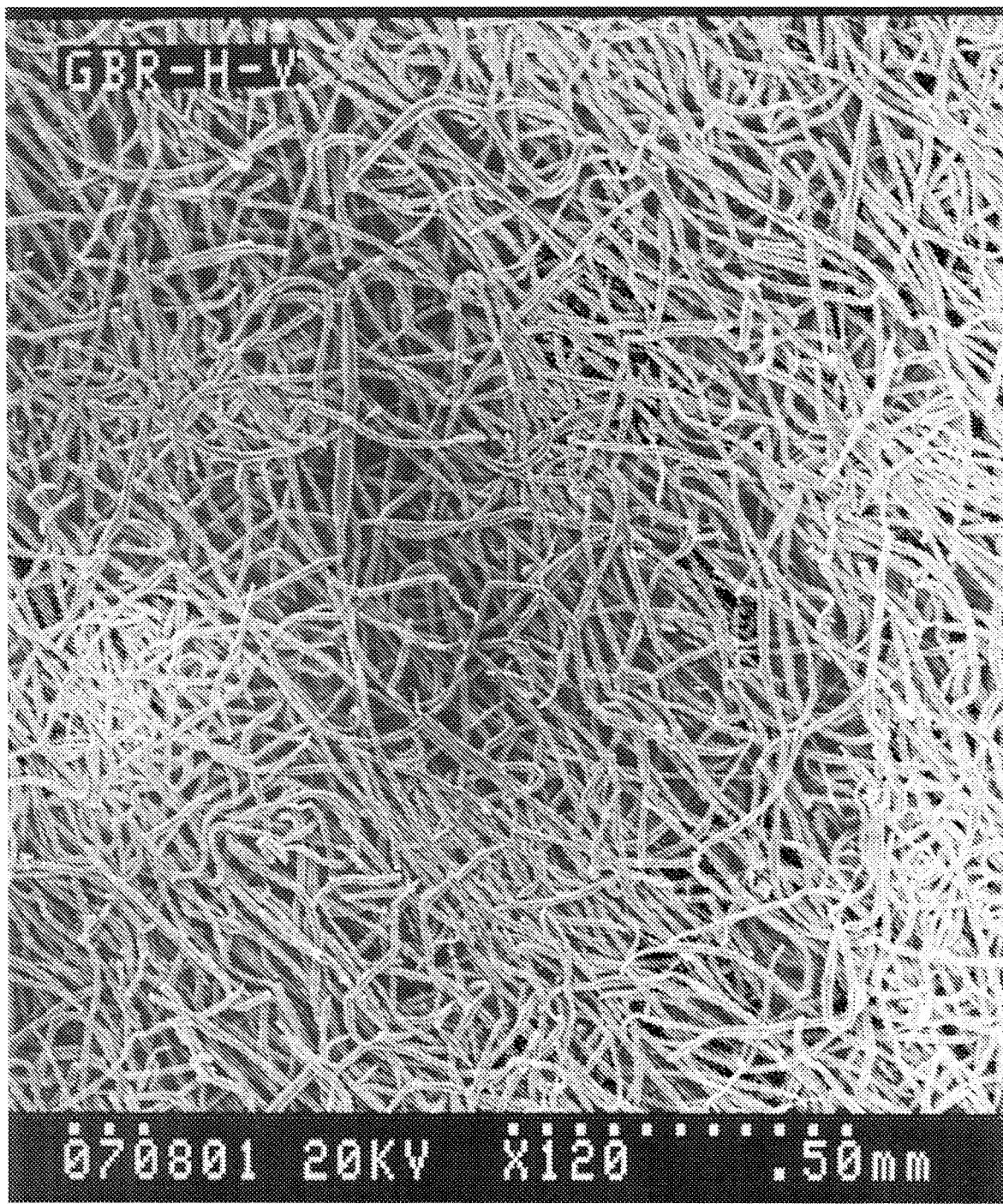
FIG. 4 is a scanning electron micrograph of a surface of a Si—CaCO$_3$/PLA layer prepared in Example 2.
Figure 5:
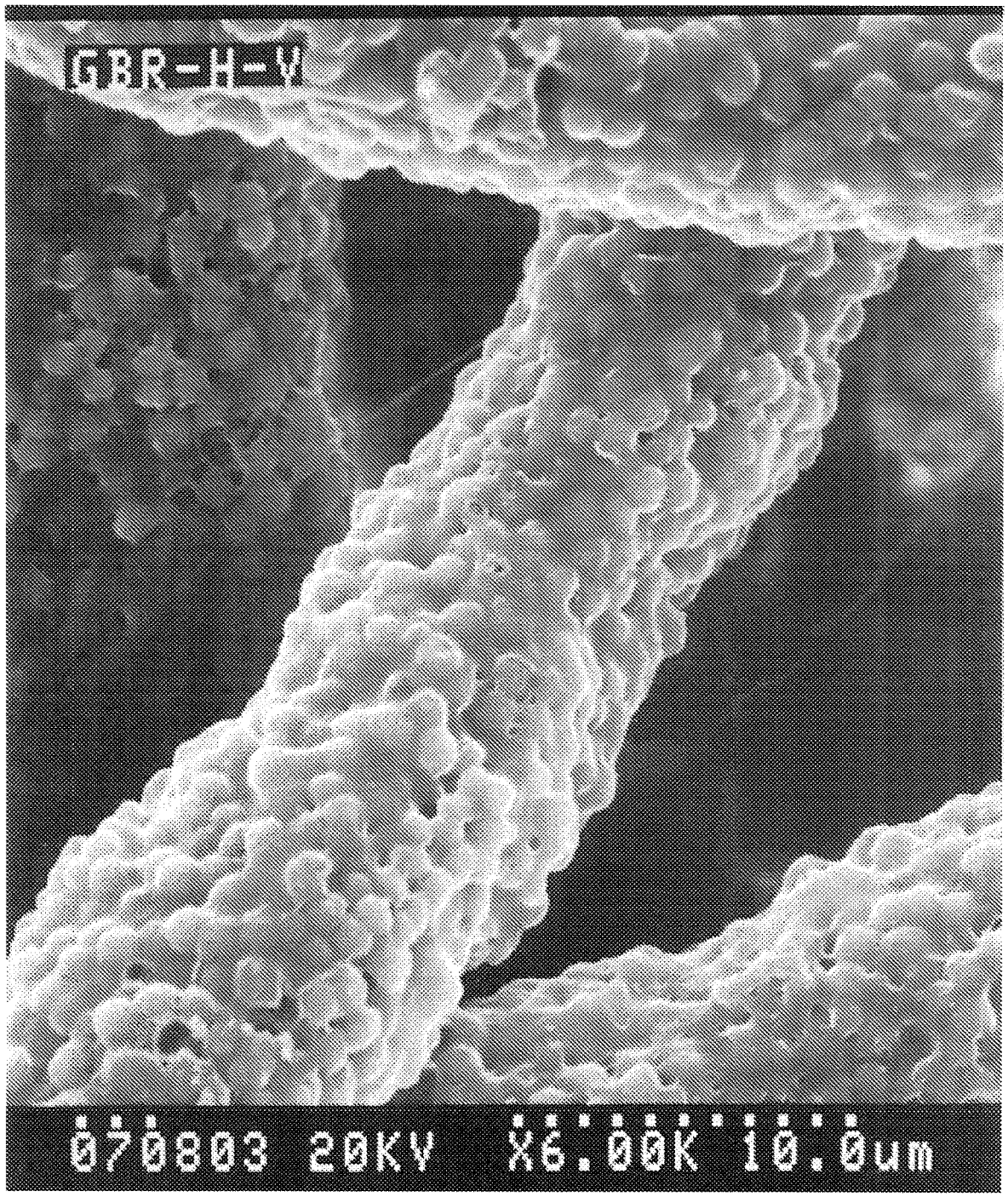
FIG. 5 is a scanning electron micrograph of fibers configuring the Si—CaCO$_3$/PLA layer prepared in Example 2.

The scanning electron micrographs of the PLA layer surface and of the Si—CaCO$_3$/PLA layer surface are shown in FIG. 3 and FIG. 4, respectively. A scanning electron micrograph of fibers forming the Si—CaCO$_3$/PLA layer is shown in FIG. 5, demonstrating that Si—CaCO$_3$ particles are attached to PLA fibers.

Figure 6:
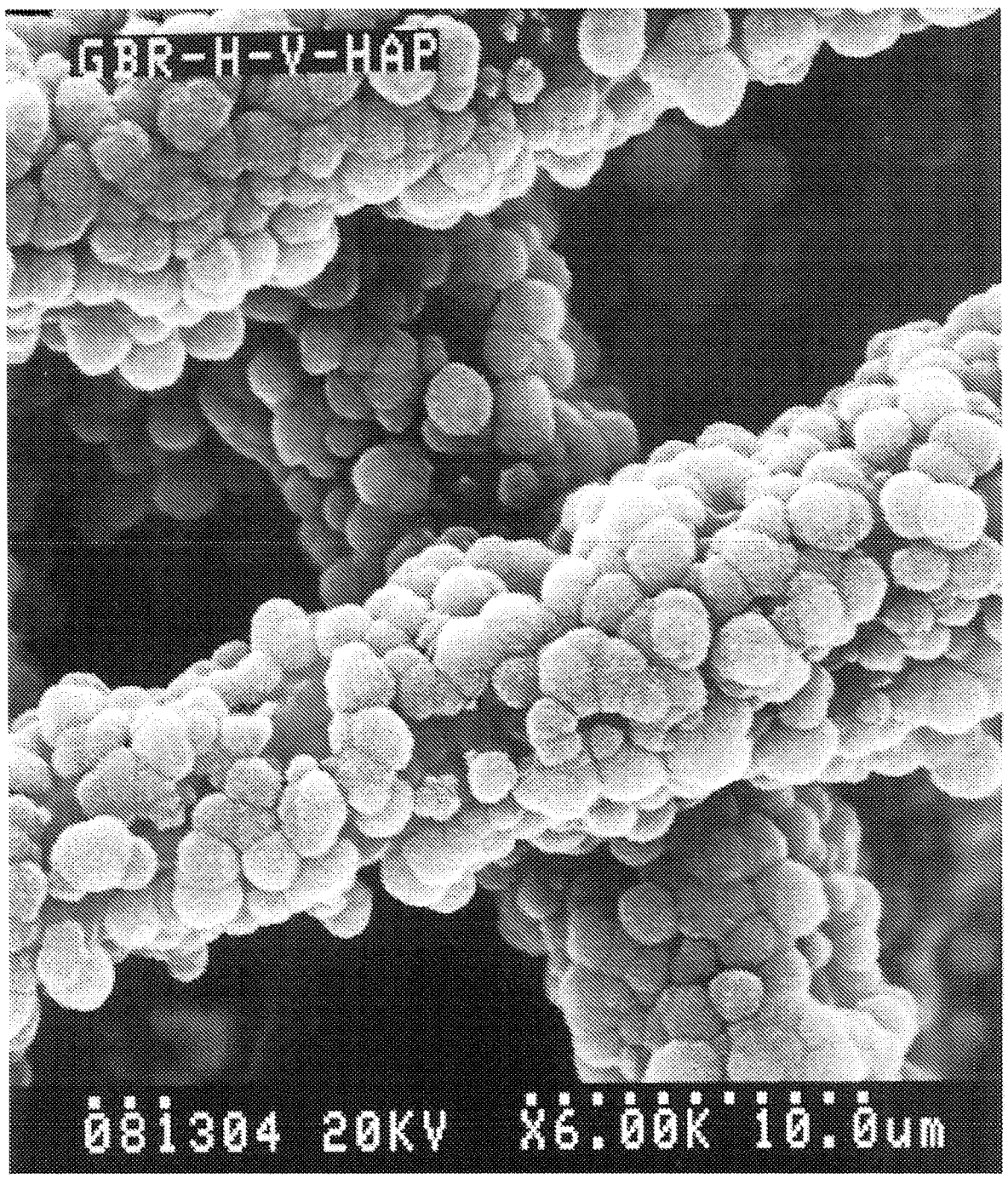
FIG. 6 is a scanning electron micrograph of fibers configuring the Si—CaCO$_3$/PLA layer after soaking a composite membrane prepared in Example 2 in 1.5 SBF.
Figure 7:
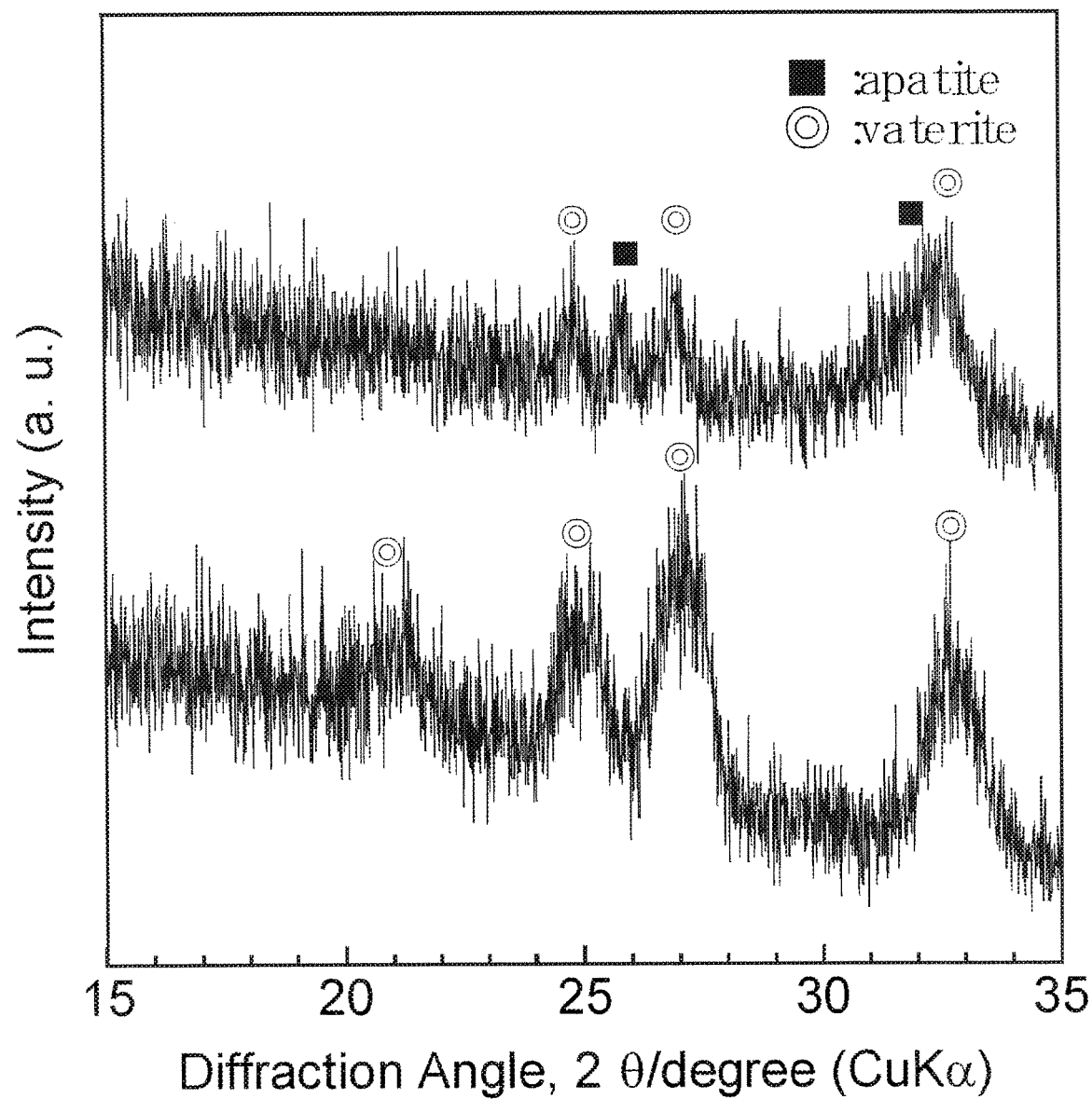
FIG. 7 depicts X-ray diffraction patterns of the composite membrane prepared in Example 2, before and after soaking in 1.5SBF.

The Si—CaCO$_3$/PLA layer surface of the resulting composite membrane was brought into contact with 1.5SBF at 37° C. for one day. The scanning electron micrograph of fibers on the side in contact with 1.5SBF is shown in FIG. 6, demonstrating that a substance quite different from Si—CaCO$_3$ covers the surface of fibers, as compared to FIG. 5. The X-ray diffraction patterns before and after soaking in 1.5SBF are shown in FIG. 7, indicating that peaks of apatite appear after the soaking. These results indicate that the Si—CaCO$_3$/PLA layer surface is coated with apatite.

Bone reconstruction ability of a guided bone regeneration material of the present invention was evaluated. The evaluation was performed by observing and comparing the increase of cells per 1 cm$^2$ after inoculation of osteoblastic cells on the apatite-coated Si—CaCO$_3$/PLA layer surface (Si-composite), on the PLA layer surface (PLA), or on a control (Thermanox: plastic disc for cell culture which has been treated on its surface), and soaking the surfaces of these into wells which are filled with culture medium, respectively.

Experimental Conditions

Cultivation of cells: 24-well plate was used.
Cell type: murine osteoblastic cells (MC3T3-E1 cells: Riken Institute of Physical and Chemical Research) was used.
Cellular inoculation number: 1×10$^4$ cells/well.
Medium: α-MEM (containing 10% fetal bovine serum).
Medium exchange: on the day following the inoculation, thereafter every other day.
Cell counting method: The measurement was performed using the Cell Counting Kit-8 (cellular growth/cellular toxicity analytical reagent; Dojindo Laboratories) in accordance with the protocol attached to the reagent.

Figure 8:
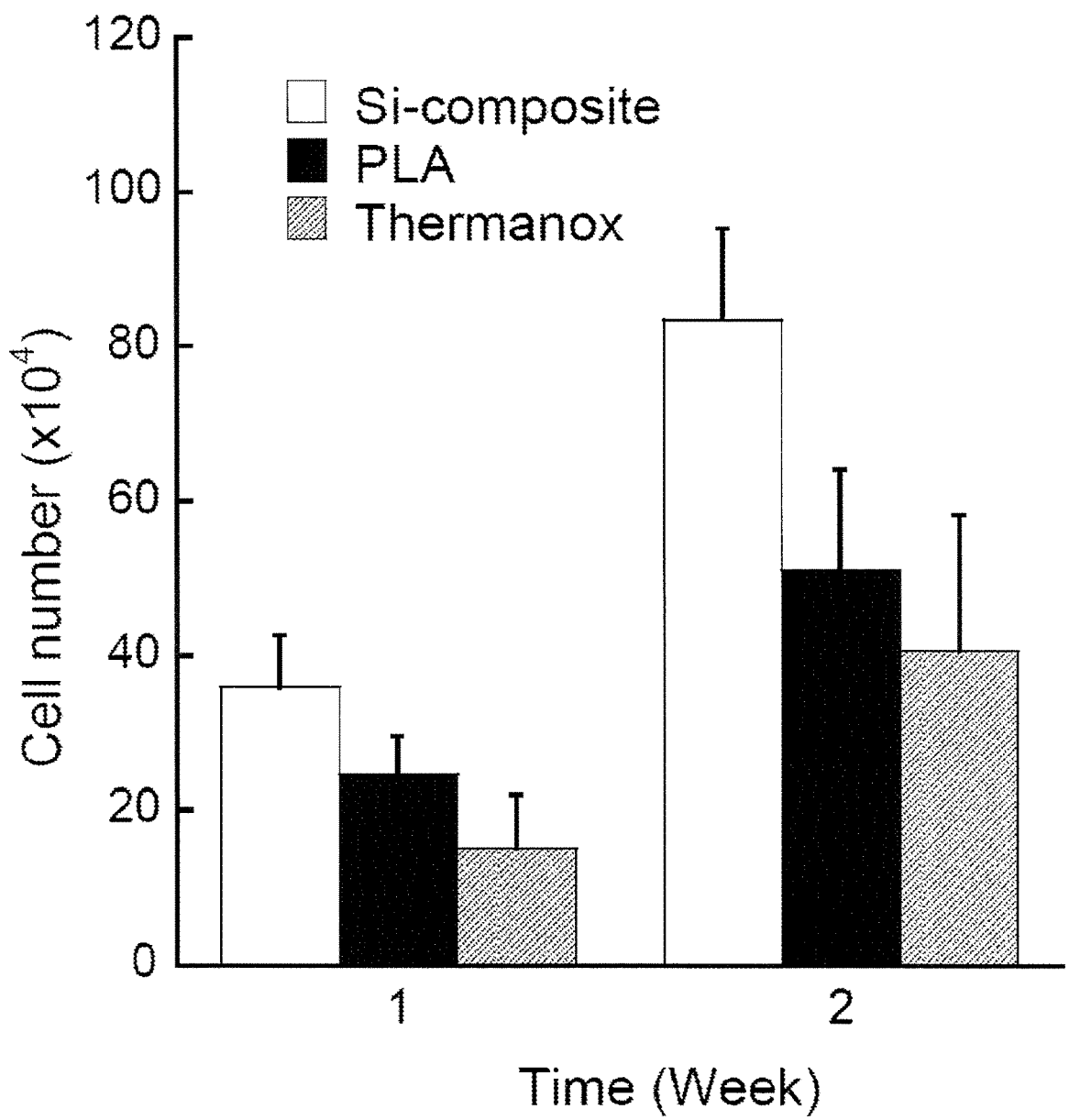
FIG. 8 is a graph for the evaluation of the cellular affinity of the Si—CaCO$_3$/PLA layer and PLA layer prepared in Example 2.

FIG. 8 shows changes in the number of cells on an apatite-coated Si—CaCO$_3$/PLA layer surface (Si-composite), on a PLA layer surface (PLA), and on a control in terms of cells per 1 cm$^2$. The data in FIG. 8 demonstrate that the surface of the layer incorporating the novel mechanism (Si—CaCO$_3$) gives significantly higher growth capability of osteoblasts proliferation than the surface of PLA layer and control. From this result, guided bone regeneration material of the present invention is expected to become an excellent bioresorbable GBR material that excels in bone reconstruction ability.

While the above description is of the preferred embodiments of the present invention, it should be appreciated that the invention may be modified, altered, or varied without deviating from the scope and fair meaning of the following claims.

What is claimed is:

1. A method for producing a fibrous biodegradable bone regeneration material by using an electrospinning process, comprising:

kneading a mixture of biodegradable polymer by using a kneader to produce a composite, wherein the mixture comprises a biodegradable polymer and calcium compound particles;

dissolving the composite in chloroform having a purity of 99% or more to produce a spinning solution having a polymer content of 4 to 12 wt %;

feeding the spinning solution to a nozzle of an electrospinning apparatus at a predetermined rate;

spinning a biodegradable fiber from the nozzle toward a collector of the electrospinning apparatus by applying a high voltage to the nozzle to convert the spinning solution into the biodegradable fiber in an electric field between the nozzle and the collector while evaporating the chloroform, wherein the calcium compound particles are distributed in the fiber; and collecting the fibers deposited on the collector.

2. The method of claim 1, wherein the biodegradable polymer comprises poly(lactic-acid).

3. The method of claim 1, wherein the biodegradable polymer comprises a copolymer of poly(lactic-acid) and poly(glycolic acid).

4. The method of claim 1, wherein the calcium compound particles comprise silicon releasing calcium carbonate.

5. The method of claim 1, wherein the calcium compound particles comprise tricalcium phosphate.

6. The method of claim 1, wherein a content of the calcium compound in the composite is 40-60 wt %.

7. A fibrous biodegradable bone regeneration material produced by a process comprising:

kneading a mixture of biodegradable polymer by using a kneader to produce a composite, wherein the mixture comprises a biodegradable polymer and calcium compound particles;

dissolving the composite in chloroform having a purity of 99% or more to produce a spinning solution having a polymer content of 4 to 12 wt %;

feeding the spinning solution to a nozzle of an electrospinning apparatus at a predetermined rate;

spinning a biodegradable fiber from the nozzle toward a collector of the electrospinning apparatus by applying a high voltage to the nozzle to convert the spinning solution into the biodegradable fiber in an electric filed between the nozzle and the collector while evaporating the chloroform; and collecting the biodegradable fiber deposited on the collector.

8. The fibrous biodegradable bone regeneration material of claim 7, wherein the biodegradable polymer comprises poly(lactic-acid).

9. The fibrous biodegradable bone regeneration material of claim 7, wherein the biodegradable polymer comprises a copolymer of poly(lactic-acid) and poly(glycolic acid).

10. The fibrous biodegradable bone regeneration material of claim 7, wherein the calcium compound particles comprise silicon releasing calcium carbonate.

11. The fibrous biodegradable bone regeneration material of claim 7, wherein the calcium compound particles comprise tricalcium phosphate.

12. The fibrous biodegradable bone regeneration material of claim 7, wherein a content of the calcium compound in the composite is 40-60 wt %.

* * * * *